United States Patent

Nilson

[11] Patent Number: 6,116,468
[45] Date of Patent: Sep. 12, 2000

[54] ARRANGEMENT AND METHOD FOR DISPENSING PRESERVATIVE-FREE NASAL SPRAYS AND SIMILAR PREPARATIONS

[75] Inventor: Kurt Nilson, Dalby, Sweden

[73] Assignee: Astra Aktiebolag, Sodertalje, Sweden

[21] Appl. No.: 08/844,989

[22] Filed: Apr. 23, 1997

Related U.S. Application Data

[62] Division of application No. 08/347,405, filed as application No. PCT/SE93/00485, Oct. 28, 1993, abandoned.

[30] Foreign Application Priority Data

Jun. 3, 1992 [SE] Sweden .................................. 9201718

[51] Int. Cl.⁷ .................................................. B65D 47/12
[52] U.S. Cl. ........................... 222/108; 222/420; 222/562
[58] Field of Search ............... 222/108, 189.09, 222/562, 571, 420; 239/57; 604/263, 295

[56] References Cited

U.S. PATENT DOCUMENTS

| | | |
|---|---|---|
| 1,657,050 | 1/1928 | Walter .............................. 220/367.1 X |
| 1,816,442 | 7/1931 | Reefer .................................. 239/57 X |
| 2,434,875 | 1/1948 | Turnbull et al. . |
| 2,549,161 | 4/1951 | Bishop ................................. 239/57 X |
| 3,327,752 | 6/1967 | Davis .................................. 215/317 X |
| 3,330,481 | 7/1967 | Dearling . |
| 3,362,587 | 1/1968 | Postel ..................................... 222/108 |
| 3,383,018 | 5/1968 | Grimsley .................................. 222/108 |
| 3,403,809 | 10/1968 | Kennedy et al. .................... 220/367.1 |
| 3,837,574 | 9/1974 | Curran ..................................... 239/57 |
| 3,955,710 | 5/1976 | Commisso ...................... 220/367.1 X |
| 4,463,880 | 8/1984 | Kramer et al. ...................... 222/420 X |
| 4,708,851 | 11/1987 | Freytag Von Loringhoven ... 239/57 X |
| 4,726,519 | 2/1988 | Muoio . |
| 4,938,389 | 7/1990 | Rossi et al. ......................... 222/420 X |
| 5,074,440 | 12/1991 | Clements et al. .................. 222/189.09 |
| 5,105,993 | 4/1992 | La Haye et al. .................... 222/420 X |
| 5,207,657 | 5/1993 | Gibilisco ............................ 222/420 X |
| 5,219,101 | 6/1993 | Matkovich et al. ................ 222/420 X |
| 5,232,127 | 8/1993 | Trotta et al. ............................ 222/108 |

FOREIGN PATENT DOCUMENTS 0 131 501 A1 1/1985 European Pat. Off. .
0 218 840 A2 9/1985 European Pat. Off. .
0 170 198 A2 5/1986 European Pat. Off. .

*Primary Examiner*—Kenneth Bomberg
*Attorney, Agent, or Firm*—Fish & Richardson P.C.

[57] ABSTRACT

The invention relates to a method for keeping the dispensing parts on a device for administering a sterile preparation for local treatment containing a preservative-free preparation free from bacterial growth. This is achieved in that the dispensing part is allowed to dry quickly after each use. The invention is also directed towards a cap to be used in this method.

29 Claims, 3 Drawing Sheets

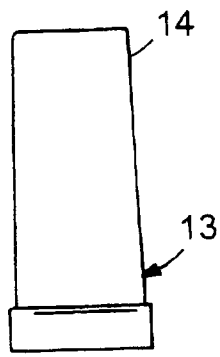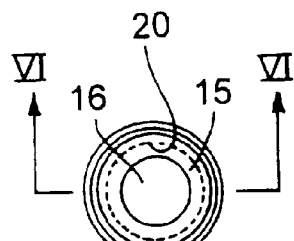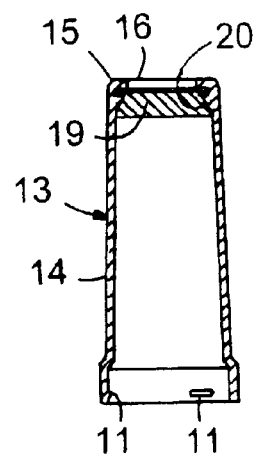
FIG. 6A  FIG. 6B  FIG. 6C
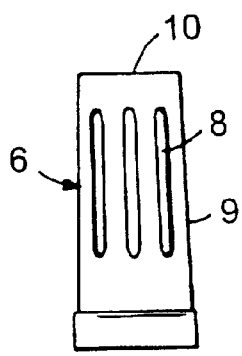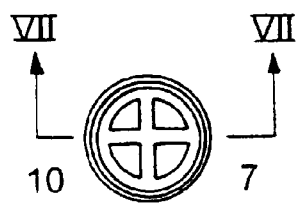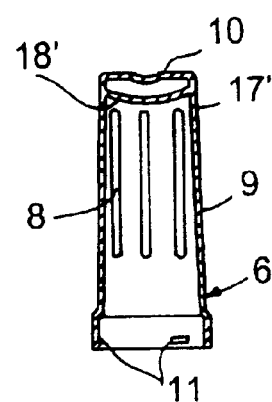
FIG. 7A  FIG. 7B  FIG. 7C
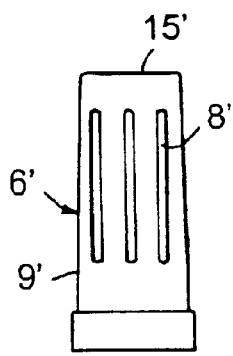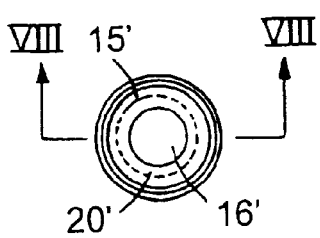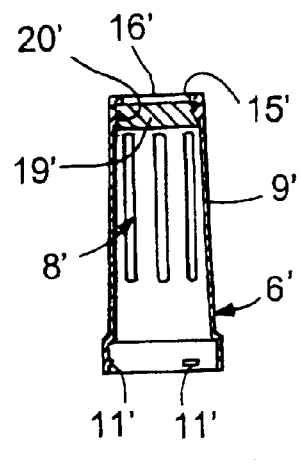
FIG. 8A  FIG. 8B  FIG. 8C

ARRANGEMENT AND METHOD FOR DISPENSING PRESERVATIVE-FREE NASAL SPRAYS AND SIMILAR PREPARATIONS This is a divisional of application Ser. No. 08/347,405, filed Dec. 2, 1994, now abandoned, which is a National Stage application of PCT/SE93/00485, filed Oct. 28, 1993.

FIELD OF THE INVENTION

The present invention relates to devices for administering liquid, sterile preparations for local treatment, such as nasal sprays and eye drops and more particularly to an arrangement and a method for facilitating the use of sterile preparations not containing preservatives.

BACKGROUND OF THE INVENTION

Nasal sprays are usually administered by means of a bottle made of plastic or glass or another equivalent receptacle containing a solution to be sprayed into the nostril. The bottle is provided with a part for dispensing the preparation to the location to be inserted into the nostril. The solution then is squirted into the nostril by any suitable means, for instance by means of a pump, by deformation of the bottle or by utilizing a suitable propellant. After use the olive is covered by a cap in order to protect the olive from damages, dirt and contamination.

After use, a small amount of the solution and possibly some mucus from the nostril usually remains on the olive. These remains may form a base for the growth of bacteria and other undesirable microorganisms, since the solution not necessarily must be an antiseptic solution and sometimes even contains ingredients that may serve as nutrients for the bacteria. These bacteria then will be introduced into the nostril next time the nasal spray device is used, by the same user or by another. This of course is undesirable. The bacteria may also contaminate the contents of the bottle since there may be a direct connection between the olive and the interior of the bottle, at least during some stage of the use.

To avoid these problems normally a preservative intended to prevent the growth of bacteria is added to the solution. This however has other disadvantages, among others the inhibitory effects on cilia movement, granolyte chemotaxis or that the user may have a low tolerance against the preservatives normally used or against antiseptic agents or additives in general. Therefore it is desirable to provide nasal sprays which are free from preservatives and similar additives.

There are similar problems relating to the dispensing of eye drops, since it is essential that eye drops are sterile when administered to the eye.

BRIEF DESCRIPTION OF THE INVENTIVE CONCEPT

The solution of this problem as envisaged by the present invention is to provide a method which allows the part for dispensing the preparation to dry quickly as well as to provide a protective cap for said part which allows the part to dry quickly, as set forth in the appended claims. It has been found that it is sufficient to keep the part in question dry in order to keep it free from bacterial growth. By this means the part can be kept free to a degree which is sufficient in the context even if the preparation does not contain any preservatives.

SHORT DESCRIPTION OF THE DRAWINGS

Figure 3A:
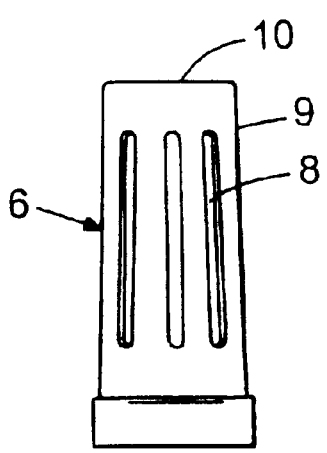
Figure 3B:
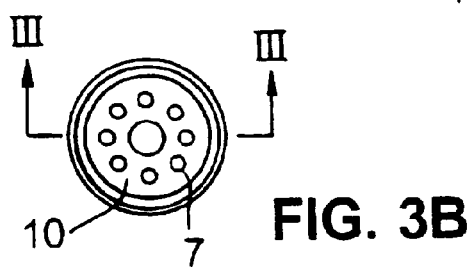
Figure 3C:
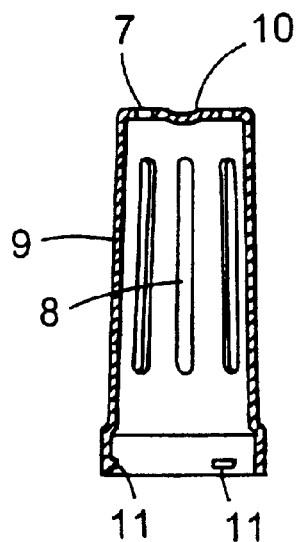
Figure 4A:
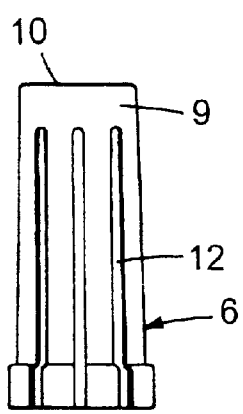
Figure 4C:
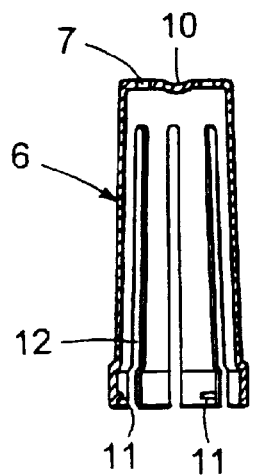
Figure 4B:
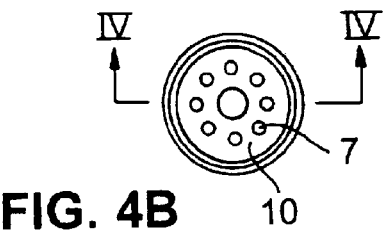
Figure 5A:
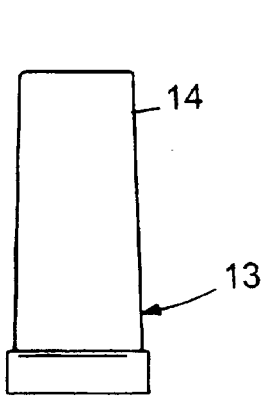
Figure 5C:
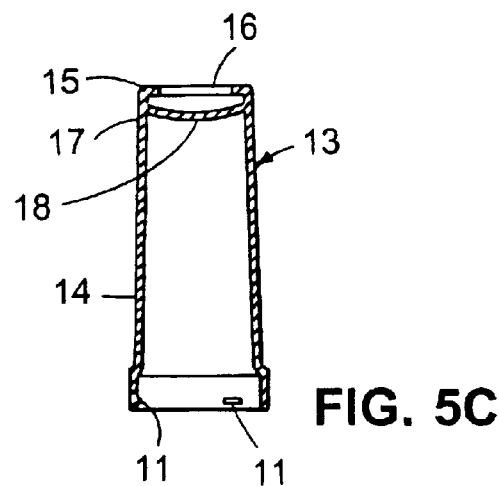
Figure 5B:
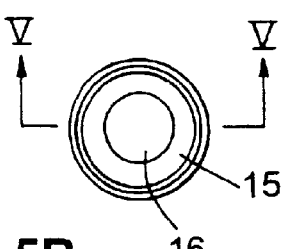

FIG. 3a illustrates a first embodiment of a protective cap according to the invention in a side view, FIG. 3b illustrates the embodiment of FIG. 3a in a top view, FIG. 3c shows a section along line III—III in FIG. 3b, FIGS. 4a–4c illustrate the embodiment of FIGS. 3a–3c in a slightly changed form in views corresponding to the views in FIGS. 3a–3c, FIGS. 5a–5c illustrate a second embodiment of a protective cap according to the invention in views corresponding to the views in FIGS. 3a–3c, FIGS. 6a–6c illustrate the embodiment of FIGS. 5a–5c in a slightly changed form in views corresponding to the views in FIGS. 3a–3c, FIGS. 7a–7c illustrate a third embodiment of a protective cap according to the invention combining the features illustrated in FIGS. 3 and 5 in views corresponding to the views in FIGS. 3a–3c, FIGS. 8a–8c illustrate a fourth embodiment of a protective cap according to the invention combining the features illustrated in FIGS. 3 and 6 in views corresponding to the views in FIGS. 3a–3c.

DETAILED DESCRIPTION OF PREFERRED EMBODIMENTS OF THE INVENTION

In the description below and in the drawings details which are identical will be designated with the same reference signs.

Figure 1:
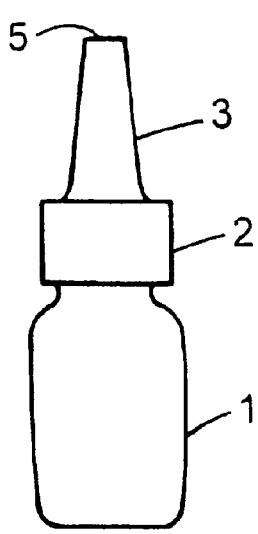
FIG. 1 illustrates a typical spray bottle for nasal sprays.
Figure 2:
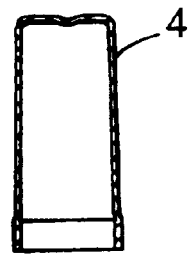
FIG. 2 illustrates a conventional protective cap for a nasal spray bottle.

FIGS. 1 and 2 illustrate a conventional device for administering a nasal spray of the kind containing a pump mechanism (not shown) for ejecting the nasal spray solution. The device comprises a bottle 1 having a closure cap 2 with a nasal tube or alive 3. The olive is covered by a protective cap 4, illustrated in FIG. 2, when the device is not in use. The protective cap is provided with a conical side wall and an end wall. The other constructional details of the device are of no particular concern in the context apart from the olive and its protective cap and are therefore not described in detail.

The outlet for the nasal solution is located at the tip of the olive (at 5). When the spray device has been used usually some droplets of nasal solution remain in the area close to the outlet. Since these droplets normally are contaminated by bacteria or similar originating from the nostril of the user, there is a great risk for an excessive growth of bacteria in the droplets if a solution not containing a preservative is used. Nasal spray solutions are normally not antiseptic.

The embodiment according to the invention illustrated in FIGS. 3a–3c comprises a protective cap 6 which substantially has the shape of a truncated cone with a small top angle. The protective cap 6 is provided with beads or lugs 11 for securing the cap to the closure cap 2. A typical size of the cap may be as follows: Height 29 mm, Base diameter 13 mm and Top diameter 11 mm, giving a total outside area of 1100 mm$^2$. The surface 9 of the cap is provided with longitudinal slits 8. To facilitate the air circulation through the slits and around the olive, the end wall 10 of the cap is provided with axial holes or vents 7. Consequently the olive will dry quickly when the cap has been replaced after use since the air has free access to the olive. As mentioned above, the conditions for bacterial growth are unfavourable when the olive is dry.

In a protective cap of the size described above it is preferred that the total area of the slits and the holes is at least 50 mm², i.e. a ratio of about 1:26, preferably 1:22 relative to the outer surface.

In a slightly changed embodiment illustrated in FIGS. 4a–4c, the protective cap 6 is provided with longitudinal slits 12 extending all the way down to the base of the protective cap. Apart from this feature, which further enhances the circulation of air around the nasal olive, this embodiment is identical with the embodiment described above in connection with FIGS. 3a–3c.

FIGS. 5 and 6 illustrate embodiments not utilizing longitudinal slits. The embodiment according to FIGS. 5a–5c comprises a protective cap 13 with an unbroken side wall 14. The cap is provided with an end wall 15 having a central opening 16. An annular, circumferential bead 17 is arranged on the inside wall of the cap a slight distance from the opening 16. A porous, absorbent, comparatively thin and slightly concave disc 18 having a diameter which is slightly larger than the inside diameter of the cap adjacent the bead 17 is snapped into place past the bead. The disc 18 will in this way be held under tension by means of the bead 17 and the part of the inside of the wall located above the bead 17. The bead 17 is located such a distance away from the end wall 15 that the disc 18 comes into direct contact with the tip 5 of the olive 3 when the protective cap is placed on the bottle. Any liquid on the tip of the olive then will be absorbed by the disc by means of capillary forces. In this way the liquid will be distributed over a large area which means that the liquid will evaporate quickly. In this way the olive will be kept effectively dry. This is essential in order to prevent growth of contaminating bacteria, particularly bacteria being Gram-negative. Examples of suitable absorbents are cellulose in different forms such as filtering paper, cigarette filters, sponges or cotton, and different plastics materials in the form of woven or non-woven fibers or in the form of sponges, such as polyamides, polyvinylacetate, polyesters.

In order to ensure that the absorbent material is kept in a proper hygienic condition, the material may be impregnated with a suitable preservative, for instance chlorhexidine acetate.

A slightly altered form of the embodiment according to FIGS. 5a–5c is illustrated in FIGS. 6a–6c. In this embodiment the disc has been replaced by an absorbent plug 19 held by projections 20. The materials of the plug may be the same and may have the same physical form and properties as the materials in the disc described above. At present ethylenevinylacetate foam or sintered polyethylene seem to be the most suitable materials. The projections 20 are not absolutely necessary, since the plug for instance can be glued to the cap or be bonded to the cap at the moulding thereof. Depending on the materials, a simple press fit also may be conceivable.

The two latter embodiments are particularly suitable in nasal spray bottles mainly intended to be carried in the users pocket, handbag or similar since these embodiments are more effective in keeping out dirt etc than the previous embodiments.

An embodiment which would belong to the same category and which essentially have the same properties as the embodiments according to FIGS. 5 and 6 is an embodiment wherein the entire protective cap is made of a fibrous, absorbent material. This embodiment is however not illustrated. An alternative embodiment would be to make the cap of a relatively rigid fibermaterial which is permeable in regard of vapour, for instance glass-fibre, felt or gauze.

FIGS. 7a–7c and 8a–8c illustrate embodiments of the invention which essentially are a combination of the embodiment according to FIGS. 3a–3c with the embodiments according to FIGS. 5a–5c and FIGS. 6a–6c respectively.

FIGS. 7a–7c thus illustrate a cap 6 comprising a side wall 9 provided with longitudinal slits 8, an end wall 10 provided with holes 7 as well as with beads 11. The cap 6 additionally is provided with a disc 18' mounted in a similar way as the disc 18 in the embodiment according to FIGS. 5a–5c.

FIGS. 8a–8b illustrate a cap 6' comprising a side wall 9' provided with longitudinal slits 8', an end wall 15 provided with a hole 16' as well as with beads 11'. The cap 6' furthermore is provided with lugs 20' for holding a porous plug 19'.

It is also conceivable to provide an ordinary protective cap with a desiccant, such as silica gel. In this case the cap must form an airtight seal against the bottle since the desiccant otherwise would absorb moisture from the ambient air and soon become ineffective.

As mentioned in the introduction, the basic principle also is applicable to other liquid, sterile, preservative-free preparations for local treatment that are dispensed from containers onto the place to be treated, for instance eye drops being dispensed from a plastic squeeze bottle having a dispensing spout normally covered with a protective cap when the bottle is not in use.

I claim:

1. A device for dispensing a liquid, sterile, preservative-free preparation free from bacterial growth, comprising
   a body including a reservoir for containing said liquid, sterile, preservative-free preparation and, in fluid communication with the reservoir, a dispensing part constructed to deliver said liquid preparation in a form selected from the group consisting of a plurality of droplets, a spray and a stream, directly to a predetermined region of the human body, said dispensing part having a dispensing outlet; and
   a protective cap constructed to be removably mounted over said dispensing part, said protective cap defining an opening that allows ambient air to circulate through said cap to facilitate air-drying of said dispensing part, and said cap having an absorbent material which contacts said dispensing outlet, where at least some portion of said absorbent material contacts ambient air when said cap is mounted over said dispensing part.

2. The device of claim 1 wherein said protective cap further comprises a top end wall, where said top end wall defines said opening.

3. The device of claim 2 wherein said absorbent material is located near said opening in said top end wall.

4. The device of claim 1 wherein said predetermined region comprises a human nostril.

5. The device of claim 4 wherein said dispensing part comprises an elongated tube constructed for nasal delivery, said tube including said dispensing outlet at its extremity for delivery of said liquid preparation to a nostril.

6. The device of claim 5 wherein said device is constructed to deliver said liquid preparation in the form of a spray.

7. The device of claim 1 wherein said predetermined region comprises a human eye.

8. The device of claim 7 wherein said dispensing part comprises an elongated tube constructed for delivery to a human eye, said tube including said dispensing outlet at its extremity for delivery of said liquid preparation to an eye.

9. The device of claim 8 wherein said device is constructed to deliver said liquid preparation in the form of a plurality of droplets, for dropwise delivery to the eye.

10. The device of claim 1 further comprising said liquid, sterile, preservative-free preparation, wherein said liquid preparation comprises a medicament.

11. A device for dispensing a liquid, sterile, preservative-free preparation free from bacterial growth, comprising
   a body including a reservoir for containing said liquid, sterile, preservative-free preparation and, in fluid communication with the reservoir, a dispensing part constructed to deliver said liquid preparation in a form selected from the group consisting of a plurality of droplets, a spray and a stream, directly to a predetermined region of the human body; and
   a protective cap constructed to be removably mounted over said dispensing part, said protective cap defining longitudinal slits to facilitate air-drying of the dispensing part.

12. The device of claim 11 wherein a ratio of an area of said longitudinal slit openings relative to a total area of an outer surface of said cap is about 1:22.

13. The device of claim 11 wherein said cap further comprises a top end wall, said top end wall defining an opening which allows ambient air to reach said dispensing part to facilitate air-drying of said dispensing part.

14. The device of claim 13 wherein said opening is located near a center of said top end wall.

15. The device of claim 11 wherein said predetermined region comprises a human nostril.

16. The device of claim 11 further comprising said liquid, sterile, preservative-free preparation, wherein said liquid preparation comprises a medicament.

17. The device of claim 11 wherein said cap is constructed to allow said dispensing part to deliver said liquid preparation directly to said predetermined region of the human body without prior absorption by intervening structure.

18. The device of claim 11 wherein at least a portion of said body is flexible, such that squeezing said portion of said body causes said dispensing part to deliver said liquid.

19. A device for dispensing a liquid, sterile, preservative-free preparation free from bacterial growth, comprising
   a body including a reservoir for containing said liquid, sterile, preservative-free preparation and, in fluid communication with the reservoir, a dispensing part constructed to deliver said liquid preparation, in a form selected from the group consisting of a plurality of droplets, a spray and a stream, directly to a predetermined region of the human body; and
   a protective cap constructed to be removably mounted over said dispensing part, said protective cap being shaped as a truncated cone or a pyramid comprising a top end wall, where said top end wall defines an opening near a center of said top end wall, said opening allowing ambient air to reach said dispensing part to facilitate air-drying of said dispensing part, wherein said cap further defines openings in the form of longitudinal slits.

20. A device for dispensing a liquid, sterile, preservative-free preparation free from bacterial growth, comprising
   a body including a reservoir for containing said liquid, sterile, preservative-free preparation and, in fluid communication with the reservoir, a dispensing part constructed to deliver said liquid preparation in a form selected from the group consisting of a plurality of droplets, a spray and a stream, directly to a predetermined region of the human body, said dispensing part having a dispensing outlet; and
   a protective cap constructed to be removably mounted over said dispensing part, said protective cap having a portion constructed to allow ambient air to reach said dispensing part to facilitate air-drying of said dispensing part, and said cap having an absorbent material which contacts said dispensing outlet, where at least some portion of said absorbent material contacts ambient air when said cap is mounted over said dispensing part,
   wherein said protective cap further comprises a top end wall, where said top end wall defines an opening located near a center of said top end wall which allows ambient air to reach said dispensing part to facilitate air-drying of said dispensing part.

21. A device for dispensing a liquid, sterile, preservative-free preparation free from bacterial growth, comprising
   a body including a reservoir for containing said liquid, sterile, preservative-free preparation and, in fluid communication with the reservoir, a dispensing part constructed to deliver said liquid preparation, in a form selected from the group consisting of a plurality of droplets, a spray and a stream, directly to a predetermined region of the human body; and
   a protective cap constructed to be removably mounted over said dispensing part, said protective cap being shaped as a truncated cone or a pyramid comprising a top end wall, where said top end wall defines an opening near a center of said top end wall, said opening allowing ambient air to reach said dispensing part to facilitate air-drying of said dispensing part, wherein said cap comprises an absorbent material which contacts a dispensing outlet of said dispensing part, where at least some portion of said absorbent material contacts ambient air when said cap is mounted over said dispensing part.

22. A device for dispensing a liquid, sterile, preservative-free preparation free from bacterial growth, comprising
   a body including a reservoir for containing said liquid, sterile, preservative-free preparation and, in fluid communication with the reservoir, a dispensing part constructed to deliver said liquid preparation in a form selected from the group consisting of a plurality of droplets, a spray and a stream, directly to a predetermined region of the human body, said dispensing part having a dispensing outlet; and
   a protective cap constructed to be removably mounted over said dispensing part, said protective cap having a portion constructed to allow ambient air to reach said dispensing part to facilitate air-drying of said dispensing part, and said cap having an absorbent material which contacts said dispensing outlet, where at least some portion of said absorbent material contacts ambient air when said cap is mounted over said dispensing part,
   wherein said protective cap further comprises a top end wall, where said top end wall defines an opening which allows ambient air to reach said dispensing part to facilitate air-drying of said dispensing part, said absorbent material being located near said opening in said top end wall, wherein said absorbent material comprises a flexible disc held in place by a circumferential bead, where said disc has a diameter slightly larger than a diameter of an inside portion of said cap adjacent said bead, whereby said disc is tensioned against the inside of said cap, obtaining a concave shape, a convex side of the disc being oriented towards said dispensing outlet.

23. A device for dispensing a liquid, sterile, preservative-free preparation free from bacterial growth, comprising a body including a reservoir for containing said liquid, sterile, preservative-free preparation and, in fluid communication with the reservoir, a dispensing part constructed to deliver said liquid preparation in a form selected from the group consisting of a plurality of droplets, a stray and a stream, directly to a predetermined region of the human body, said dispensing part having a dispensing outlet; and a protective cap constructed to be removably mounted over said dispensing part, said protective cap having a portion constructed to allow ambient air to reach said dispensing part to facilitate air-drying of said dispensing part, and said cap having an absorbent material which contacts said dispensing outlet, where at least some portion of said absorbent material contacts ambient air when said cap is mounted over said dispensing part, wherein said protective cap further comprises a top end wall, where said top end wall defines an opening which allows ambient air to reach said dispensing part to facilitate air-drying of said dispensing part, wherein said cap comprises a shape selected from the group consisting of a truncated cone and a pyramid, said shape including said top end wall.

24. A device for dispensing a liquid, sterile, preservative-free preparation free from bacterial growth, comprising a body including a reservoir for containing said liquid, sterile, preservative-free preparation and, in fluid communication with the reservoir, a dispensing part constructed to deliver said liquid preparation in a form selected from the group consisting of a plurality of droplets, a spray and a stream, directly to a predetermined region of the human body; and a protective cap constructed to be removably mounted over said dispensing part, said protective cap defining longitudinal slits to facilitate air-drying of the dispensing part, said cap further comprises a top end wall, said top end wall defining an opening which allows ambient air to reach said dispensing part to facilitate air-drying of said dispensing part, wherein said cap comprises a shape selected from the group consisting of a truncated cone and a pyramid, said shape including said top end wall.

25. A device for dispensing a liquid, sterile, preservative-free preparation free from bacterial growth, comprising a body including a reservoir for containing said liquid, sterile, preservative-free preparation and, in fluid communication with the reservoir, a dispensing part constructed to deliver said liquid preparation in a form selected from the group consisting of a plurality of droplets, a spray and a stream, directly to a predetermined region of the human body; and a protective cap constructed to be removably mounted over said dispensing Dart, said protective cap defining longitudinal slits to facilitate air-drying of the dispensing part, wherein said predetermined region comprises a human eye.

26. The device of claim 25 wherein said dispensing part comprises an elongated tube constructed for delivery to a human eye, said tube having an outlet at its extremity for delivery of said liquid preparation to an eye.

27. The device of claim 26 wherein said device is constructed to deliver said liquid preparation in the form of a plurality of droplets, for dropwise delivery to the eye.

28. A device for dispensing a liquid, sterile, preservative-free preparation free from bacterial growth, comprising a body including a reservoir for containing said liquid, sterile, preservative-free preparation and, in fluid communication with the reservoir, a dispensing part constructed to deliver said liquid preparation in a form selected from the group consisting of a plurality of droplets, a spray and a stream, directly to a predetermined region of the human body; and a protective cap constructed to be removably mounted over said dispensing part, said protective cap defining longitudinal slits to facilitate air-drying of the dispensing part, wherein said predetermined region comprises a human nostril, and said dispensing part comprises an elongated tube constructed for nasal delivery, said tube having an outlet at its extremity for delivery of said liquid preparation to a nostril.

29. The device of claim 28 wherein said device is constructed to deliver said liquid preparation in the form of a spray.

* * * * *

UNITED STATES PATENT AND TRADEMARK OFFICE
CERTIFICATE OF CORRECTION

PATENT NO.    : 6,116,468
DATED         : SEPTEMBER 12, 2000
INVENTOR(S)   : KURT NILSON

It is certified that error appears in the above-identified patent and that said Letters Patent is hereby corrected as shown below:

Column 1, line 21: after "location" insert "to be treated, normally a nasal tube or olive which is".

Signed and Sealed this

First Day of May, 2001

Attest:

NICHOLAS P. GODICI

Attesting Officer     Acting Director of the United States Patent and Trademark Office